United States Patent [19]

Rubin et al.

[11] Patent Number: 5,382,707
[45] Date of Patent: Jan. 17, 1995

[54] INTEGRATED MTBE PROCESS

[75] Inventors: Jacob N. Rubin, Newton Hglds.; Johannes C. Norenburg, Marblehead, both of Mass.

[73] Assignee: Stone & Webster Engineering Corp., Boston, Mass.

[21] Appl. No.: 246,579

[22] Filed: May 20, 1994

Related U.S. Application Data

[63] Continuation of Ser. No. 42,477, Apr. 2, 1993, abandoned, which is a continuation-in-part of Ser. No. 1,101, Jan. 6, 1993, abandoned.

[51] Int. Cl.$^6$ .................................. C07C 41/06
[52] U.S. Cl. ................................................ 568/697
[58] Field of Search ........................................ 568/697

[56] References Cited

U.S. PATENT DOCUMENTS

| | | | |
|---|---|---|---|
| 3,940,450 | 2/1976 | Lee | 260/614 |
| 4,148,695 | 4/1979 | Lee et al. | 203/63 |
| 4,176,141 | 11/1979 | Dixon | 585/314 |
| 4,191,845 | 3/1980 | Rubin et al. | 585/253 |
| 4,198,530 | 4/1980 | Wentzheimer et al. | 568/697 |
| 4,329,516 | 5/1982 | Al-Muddarris | 568/697 |
| 4,440,963 | 4/1984 | Childs | 568/697 |
| 4,482,775 | 11/1984 | Smith, Jr. | 585/671 |
| 4,490,563 | 12/1984 | Van Pool et al. | 568/697 |
| 4,510,336 | 4/1985 | Hearn | 568/697 |
| 4,513,153 | 4/1985 | Sandrin | 568/697 |
| 4,548,913 | 10/1985 | Schwerdtel et al. | 502/68 |
| 4,581,474 | 4/1986 | Hutson, Jr. et al. | 568/697 |
| 4,661,209 | 4/1987 | Berg | 203/51 |
| 4,754,078 | 6/1988 | Vora et al. | 568/697 |
| 4,778,943 | 10/1988 | Sun | 585/671 |
| 4,792,639 | 12/1988 | Masilamani et al. | 568/697 |
| 4,950,803 | 8/1990 | Smith, Jr. et al. | 568/697 |
| 4,975,097 | 12/1990 | Harandi et al. | 44/77 |
| 5,003,124 | 3/1991 | Smith, Jr. et al. | 585/526 |
| 5,023,389 | 6/1991 | Grandvallet et al. | 585/304 |
| 5,024,679 | 6/1991 | Harandi et al. | 44/449 |
| 5,107,047 | 4/1992 | Del Rossi et al. | 585/666 |
| 5,113,023 | 5/1992 | Anderson | 568/697 |
| 5,146,033 | 9/1992 | Schrock et al. | 585/647 |
| 5,160,414 | 11/1992 | Lee et al. | 203/57 |

FOREIGN PATENT DOCUMENTS

| | | | |
|---|---|---|---|
| 0508008 | 10/1992 | European Pat. Off. | C07C 5/27 |
| 0474188 | 3/1993 | European Pat. Off. | C07C 5/52 |
| 2520356 | 7/1983 | France | C07C 11/09 |
| 2614297 | 10/1988 | France | C07C 41/06 |
| 2121407 | 12/1983 | United Kingdom | C07C 41/06 |
| 2121791 | 1/1984 | United Kingdom | 568/697 |

Primary Examiner—Howard T. Mars
Attorney, Agent, or Firm—Hedman, Gibson & Costigan

[57] ABSTRACT

There is provided a novel integrated process for producing methyl tertiary butyl ether from a $C_4$ containing hydrocarbon feedstock comprising passing the feedstock through zones of butadiene hydrogenation, MTBE synthesis, paraffin/olefin separation and skeletal isomerization.

34 Claims, 4 Drawing Sheets

FIG. I

INTEGRATED MTBE PROCESS

The present application is a continuation of application Ser. No. 08/042,477, filed Apr. 2, 1993 which is a continuation-in-part application of Ser. No. 08/001,101, filed Jan. 6, 1993, both now abandoned.

FIELD OF THE INVENTION

The present invention relates to a process for the production of methyl tertiary butyl ether (MTBE). More particularly, the present invention relates to a process for enhancing the ultimate yield of MTBE from a process feed stream containing a mixture of $C_4$ hydrocarbons.

BACKGROUND OF THE PRESENT INVENTION

In recent years, a major technical challenge to the petroleum refining industry has been the need to establish new means for producing high octane gasolines containing oxygenates in response to pollution control regulations requiring the elimination of lead from gasoline, which was previously employed as an octane enhancer. Further, the development of more efficient, higher compression ratio gasoline engines which require higher octane fuels have spurred the industry to produce new octane enhancers.

Initially, to meet these requirements, the industry developed non-lead octane boosters and reformulated high octane gasoline to incorporate increased fractions of aromatics and branched hydrocarbons. While these and other approaches were sufficient to meet the technical requirements of regulations requiring the elimination of lead, the economic impact on the cost of gasoline was significant.

Accordingly, the industry has intensified their effort to discover new processes to manufacture the gasoline products required by the marketplace. In particular, the industry has centered on blending gasoline with lower aliphatic alkyl ethers as octane enhancers. To this end, methyl tertiary butyl ether (MTBE) has been found especially useful as an octane enhancing additive. Therefore, improvements to the processes relating to the production of MTBE have become increasingly important in the petrochemical industry.

It is known that isobutylene may be reacted with methanol over an acidic catalyst to produce MTBE. Methanol is generally in ample supply, but the supply of isobutylene is limited since it is formed only in cracking operations, primarily catalytic cracking and olefins production. Since insufficient isobutylene is available from these sources to meet the growing industry needs, many $C_4$ production facilities based on dehydrogenation of isobutane are being used to prepare isobutylene feedstocks for MTBE production. See, e.g., Al-Muddarris, U.S. Pat. No. 4,329,516. However, such facilities have proven very expensive to build and operate.

It would therefore represent a notable advancement in the state of the art if a process which provided for the increased production of MTBE from available feedstocks could be developed. To this end, the present inventors have developed an integrated process for the production of MTBE from readily available mixed $C_4$ feedstocks.

SUMMARY OF THE PRESENT INVENTION

It is an object of the present invention to provide a process for the production of methyl tertiary butyl ether.

It is another object of the present invention to enhance the ultimate yield of methyl tertiary butyl ether from a process feed stream containing a variety of $C_4$ hydrocarbons.

It is still another object of the present invention to provide a process for the production of methyl tertiary butyl ether which has less equipment fouling.

It is a still further object of the present invention to provide a more economic method of producing methyl tertiary butyl ether.

DETAILED DESCRIPTION OF THE PRESENT INVENTION

The present invention provides for the production of MTBE from a $C_4$ feedstock obtained from a catalytic cracking unit and/or an olefins production unit or mixtures thereof by conducting the following process steps, in any sequence: butadiene hydrogenation, MTBE synthesis, paraffin/olefin separation and skeletal isomerization with recycle to the MTBE synthesis or butadiene hydrogenation unit.

The present inventors have found that while each of these individual process steps are known in the art in their broadest sense, the use of these process steps in combination to produce MTBE is not taught or suggested by the prior art. Surprisingly, the present invention provides an unexpected significant increase in yield of MTBE from the $C_4$ feedstock. Further, in a preferred embodiment, by conducting the process steps of the present invention in the sequence of butadiene hydrogenation, MTBE synthesis, paraffin/olefin separation and skeletal isomerization, still further benefits are obtained.

However, depending upon the particular chemistry of the individual process steps, the sequence of the steps can be varied. For example, the chemistry of the skeletal isomerization step involves a number of competing reactions occurring simultaneously, such as: (1) the isomerization of butene-2 to isobutylene; (2) the isomerization of butene-2 to butene-1; (3) dimerization of butene-1 and butene-2 to various $C_8$ olefins; (4) transalkylation of normal butenes to produce propylene and $C_5$ olefins; (5) hydrogen transfer which results in the formation of n-butane; (6) polymerization which produces gasoline and distillate constituents; and (7) cracking with produces low molecular weight gas and coke. Thus, depending upon the catalyst system employed in the skeletal isomerization step, the compositional make-up of the effluent from the skeletal isomerization reactor will vary significantly. Accordingly, the integration of the various process steps can be altered to accommodate the change in chemistry in the skeletal isomerization unit.

Employing the process steps of the present invention, substantially all of the normal butene compounds are ultimately converted to MTBE, $C_4$ paraffins which are non-reactive, can be effectively purged from the process stream; butadienes and acetylenes are converted to butene feedstock and are eliminated upstream of the MTBE synthesis, paraffin/olefin separation and skeletal isomerization units preventing fouling and coking from occurring; and the need for employing a light ends distillation column within the skeletal isomerization unit is eliminated.

The present invention will be described in more detail hereinbelow with reference to a preferred sequence of process steps. However, it is to be understood that other sequences of process steps may be employed in the practice of the present invention.

Figure 1:
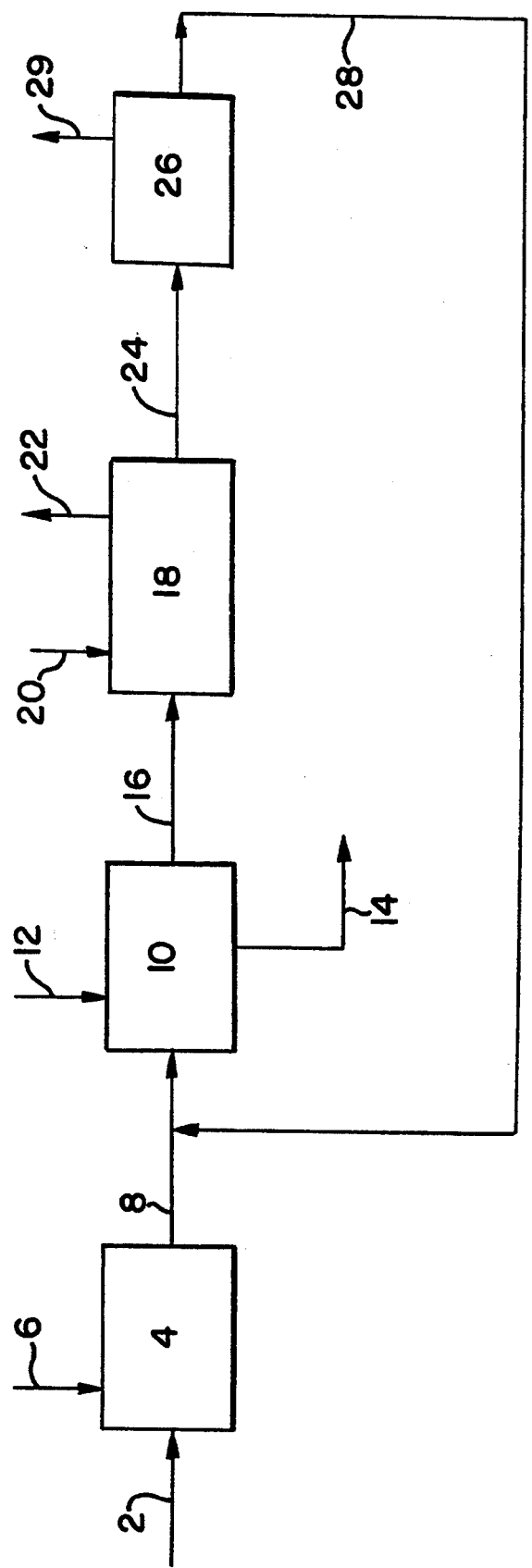
FIG. 1 depicts in flow chart format a preferred integrated process for the production of MTBE of the present invention.

Referring to FIG. 1, a $C_4$ feedstock in a line 2 is first fed to a hydroisomerization unit 4. Alternatively, the hydroisomerization unit can comprise any butadiene hydrogenation unit known to those of ordinary skill in the art which converts butadiene to butenes, such as a hydroisomerization unit or selective hydrogenation unit. Preferred is a hydroisomerization unit which in addition to converting butadiene to butenes also isomerizes at least a portion of the butene-1 component to the butene-2 components. The hydroisomerization unit 4 is fed with hydrogen by a line 6. The $C_4$ feedstock is typically a mixed $C_4$ feedstock from either a catalytic cracking or olefins production process, or mixtures thereof, and which comprises all of the $C_4$ isomers (acetylenes, dienes, olefins and paraffins), and small quantities of $C_3$ and $C_5$ hydrocarbons. The $C_4$ isomers are as follows: ethyl acetylene, vinyl acetylene, 1,3-butadiene, 1,2-butadiene, isobutylene, cis-2-butene, trans-2-butene, 1-butene, isobutane and n-butane. The actual composition of the $C_4$ stream will vary considerably between cracking and olefin sources and will also differ if a butadiene extraction unit is employed upstream to recover butadiene from olefins feedstock.

In the hydroisomerization unit 4, most of the acetylenes and dienes are catalytically converted to butenes and most of the 1-butene is catalytically converted to the 2-butenes, i.e., cis-2-butene and trans-2-butene, in the presence of hydrogen.

Hydroisomerization is a process which is well known to those of ordinary skill in the art and any particular hydroisomerization process may be employed. Typically, the hydroisomerization step is carried out in the presence of a catalyst comprising at least one hydrogenating metal and a moderately acidic carrier. A preferred catalyst can comprise a Group VIII metal, such as platinum, palladium and/or nickel, on a microporous crystalline silicate, such as a mordenite with a surface area of from 100 to 800 m²/g.

Suitable hydroisomerization conditions may include a temperature of from 40° to 400° C., a pressure from 1–100 bar and a space velocity from 0.5 to 20 kg hydrocarbon feed/kg catalyst hour. Preferred conditions are a mixed phase process at a temperature of from 40° to 150° C., a pressure of from 10 to 40 bar and a space velocity of from 1 to 15 kg feed/kg catalyst hour. See, e.g., Grandvallet et al., U.S. Pat. No. 5,023,389.

The effluent stream 8 from the hydroisomerization unit 4 substantially comprising isobutylene, cis-2-butene, trans-2-butene, isobutane, n-butane, unconverted 1-butene and $C_3$ and $C_5$ components is combined with recycle stream 28, described hereinbelow, and directed to an MTBE synthesis unit 10.

The synthesis of methyl tertiary butyl ether (MTBE) from isobutylene and methanol is a process which is well known to those of ordinary skill in the art and any particular synthesis process may be employed in the practice of the present invention. The general reaction scheme is set forth below.

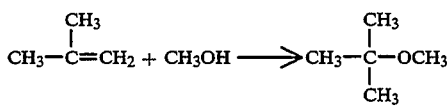

Typically, the synthesis step is carried out at mild temperatures, in the liquid phase, in the presence of a sulfonated polystyrene resin. See, Hatch and Matar, "From Hydrocarbons to Petrochemicals," Gulf Publishing Co., 1981, pp. 128–29.

The reaction usually employs an acid type ion exchange resin, such as a high molecular weight carbonaceous material containing sulfonate groups $-SO_3H$. Sulfonated resins of various types are available such as the sulfonated coals, phenol formaldehyde resins reacted with sulfuric acid, sulfonated resinous polymers of cumarone-indene with cyclopentadiene, strongly acidic cationic exchange resins such as sulfonated divinylbenzene polystyrene copolymers, and others, under various commercial names. The catalyst can be employed in a particulate solid form with sizes ranging from about 10 to about 50 U.S. sieve employing about 0.5 to 50 percent dry weight of catalyst relative to liquid content of the reactor. A fixed bed of particulate solid ion exchange resin catalyst, e.g., such as Amberlyst 15 from Rohm & Haas Co., or Dowex® M31 or M32 from Dow Chemical Co., may be employed. The same catalyst may also be employed in tubular reactors or supported in bags or other devices which permit catalytic distillation to be practiced in the reactor.

The reaction of the isobutylene with methanol can be carried out under any suitable reaction conditions. The mole ratio of methanol to isobutylene generally is in the range of about 0.05 to 10, preferably about 0.1 to 5, and still more usually about 1 to 1, at a temperature in the range of about 100° F. to about 250° F., more usually about 100° F. to 250° F., employing a pressure sufficient to maintain the reactants substantially in the liquid state, typically in the range of about 80 to 400 psig. The liquid hourly space velocity, volume of feed per volume of catalyst per hour, is preferably about 0.5 to 10.

More specific processes of MTBE synthesis are described in Childs, U.S. Pat. No. 4,440,963, Wentzheimer et al., U.S. Pat. No. 4,198,530, Masilamani et al., U.S. Pat. No. 4,792,639, Smith, Jr. et al., U.S. Pat. No. 4,950,803, Lee, U.S. Pat. No. 3,946,450 and Leum et al., U.S. Pat. No. 2,480,940.

The resultant product MTBE, along with the $C_5$ and heavier components, are withdrawn from the MTBE unit through a line 14 by fractionation, as is well known to those skilled in the art. The remaining components of the MTBE synthesis feed, the cis-2-butene, trans-2-butene, isobutane, n-butane, unconverted 1-butene and $C_3$ components are then directed through a line 16 to a paraffin/olefin separation unit. The paraffin/olefin separation can be carried out by a wide variety of separation processes known to those skilled in the art, including, but not limited to, extractive distillation, selective membrane separation and/or molecular sieve separation. Particularly suitable for use in the practice of the present invention is an extractive distillation unit 18 to remove paraffins and $C_3$ components.

Extractive distillation is a well known process, and has been employed in the past to separate butadiene from $C_4$ feedstreams, as well as other separations such as separating MTBE from cyclopentane. See, e.g., Berg, U.S. Pat. No. 4,661,209. Extractive distillation generally refers to processes where a higher boiling selective solvent is added to alter the relative volatilities of the components in the feed mixture. See, generally, Perry and Chilton, "Chemical Engineers' Handbook," McGraw Hill, 5th ed., 1973, pp. 13-43 to 13-48.

A wide variety of solvents may be employed in the extractive distillation step of the present invention, including, but not limited to, tetrahydrofuran, diethyl ketone, diethyl carbonate, methyl ethyl ketone, pentanedione, cyclopentanone, acetone, butyronitrile, acetyl piperidine, acetophenone, pyridine, diethyl oxalate, propionitrile, dimethyl acetamide, n-methyl pyrrolidone, acetonyl acetone, tetrahydrofurfuryl alcohol, dimethyl sulfolane, dimethyl cyanamide, methyl carbitol, dimethyl formamide, methyl cellosolve, furfural, acetonitrile, ethylene chlorhydrin, gamma-butyrolactone, methanol, beta-chloropropionitrile, pyrrolidone, propylene carbonate, nitromethane, ethylene diamine and mixtures of any of the foregoing. Especially preferred is acetonitrile. Further, these solvents may also be employed with a water diluent.

The solvent, in a line 20, is introduced near the top of the extractive distillation column or tower (not shown), usually a few plates from the top, and flows downward until it reaches the stillpot or reboiler. Its presence on each plate of the distillation column alters the relative volatility of the close boiling compounds to make the separation on each plate greater than would be possible without the solvent and thus requires either fewer plates to effect the same separation, makes possible a greater degree of separation with the same number of plates and also makes possible separation which could not be achieved with conventional distillation.

The light compounds, $C_3$ and lighter boiling hydrocarbons, as well as the $C_4$ paraffins isobutane and n-butane, are thereby removed from the top of the extractive distillation unit through a line 22. The bottoms from the extractive distillation are directed to a stripper (not shown) wherein the cis-2-butene, trans-2-butene and unconverted 1-butene are recovered from the overhead of the stripper, withdrawn through a line 24 and fed to the skeletal isomerization unit 26.

Skeletal isomerization is a process by which the 2-butenes, cis-2-butene and trans-2-butene, are converted to isobutylene and the 1-butene is isomerized to a 2-butene and which can then be further isomerized to isobutylene. Skeletal isomerization of olefins is known to be conducted by contacting unbranched olefins with acidic catalysts at pressures near atmospheric and temperatures ranging from about 600° to 1100° F. The isomerization of olefins is well known to be limited by the thermodynamic equilibrium of reacting species. Useful catalysts and processes are described in the patent literature, inter alia, Smith, Jr., U.S. Pat. No. 4,482,775, Sun, U.S. Pat. No. 4,778,943, Schwerdtel et al., U.S. Pat. No. 4,548,913, Del Rossi et al., U.S. Pat. No. 5,107,047 and Chih-Cheng, et al., EP 0 508 008.

Accordingly, a portion of the 2-butenes are essentially converted to isobutylene with a small amount of light and heavy hydrocarbon by-products (gasoline) and the effluent from the skeletal isomerization unit is recycled in a line 28 to the MTBE synthesis unit for conversion of the isobutylene to MTBE product. Further, the heavy hydrocarbon by-products (gasoline) can be withdrawn from the skeletal isomerization unit through a line 29.

When a relatively minor quantity of heavy hydrocarbon (gasoline) by-product is produced in the skeletal isomerization unit the heavy hydrocarbon takeoff stream 29 can be omitted and the heavy hydrocarbon can be recycled with the rest of the effluent from the skeletal isomerization unit in streams 28 to the hydroisomerization (see FIG. 4) or MTBE synthesis unit where it can be purged or removed from the process with the methyl tertiary butyl ether product stream 14.

Figure 2:
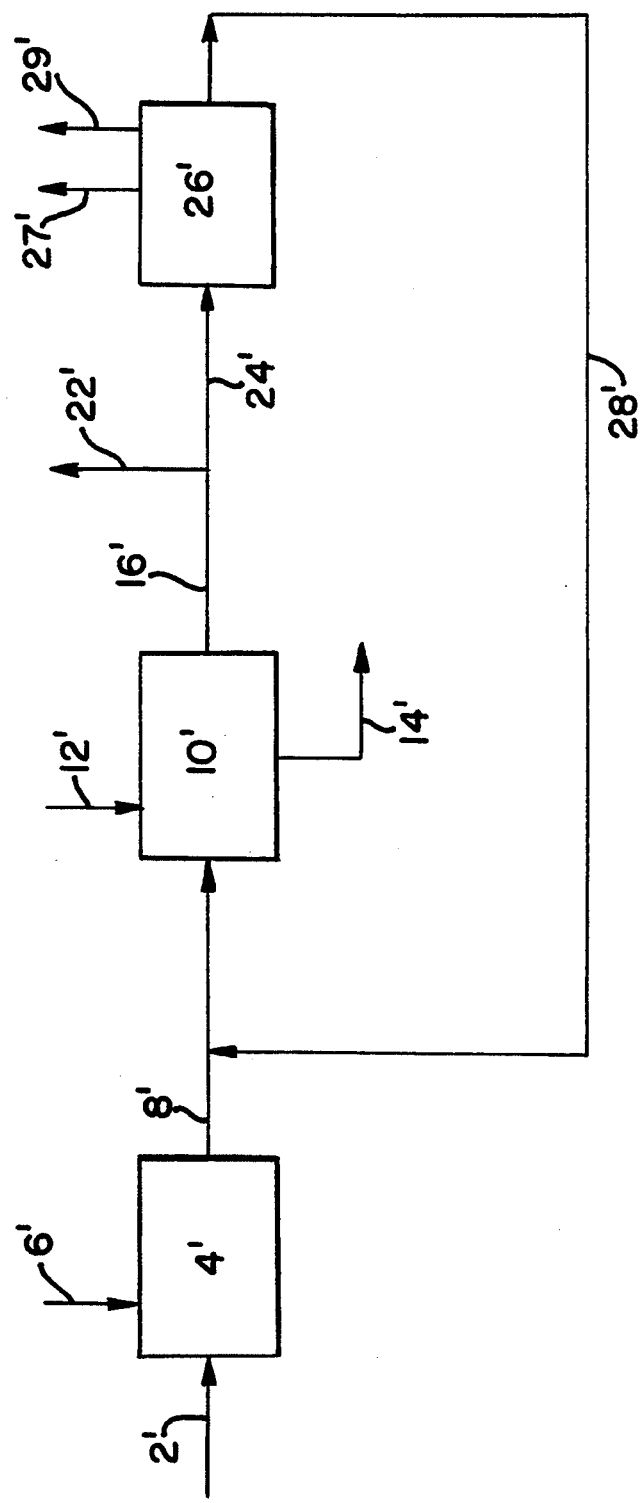
FIG. 2 depicts in flow chart format a process of the prior art which is employed in the comparative examples hereinbelow.

By employing the integrated process of the present invention, significant advantages are achieved over the teachings of the prior art. See FIG. 2. By employing the process of the present invention, catalyst fouling in the MTBE synthesis step is reduced by upstream butadiene conversion to butenes, the capital and operating costs of the extractive distillation step are reduced since the 2-butene components require less trays and utilities to effect the equivalent separation than 1-butene, fouling in the extractive distillation unit is reduced due to upstream conversion of butadiene, and the overall yield of the process is improved since additional isobutylene is available for conversion. The process of the present invention enables an operator to convert from about 80 to about 90% or greater of the entire raw $C_4$ stream derived from ethylene production plant to MTBE. Additionally, the removal of $C_5$ and heavier components in the MTBE synthesis step prevents contamination, and facilitates recovery, of the extractive solvent in the extractive distillation unit.

Further, there is no need for including a depropanizer in the skeletal isomerization process to remove light by-products. These light ends are inert in the MTBE synthesis and are removed in the extractive distillation overhead. The heavy hydrocarbon by-products (gasoline) are removed from the process stream in the MTBE product stream or via a takeoff in the skeletal isomerization unit.

Figure 3:
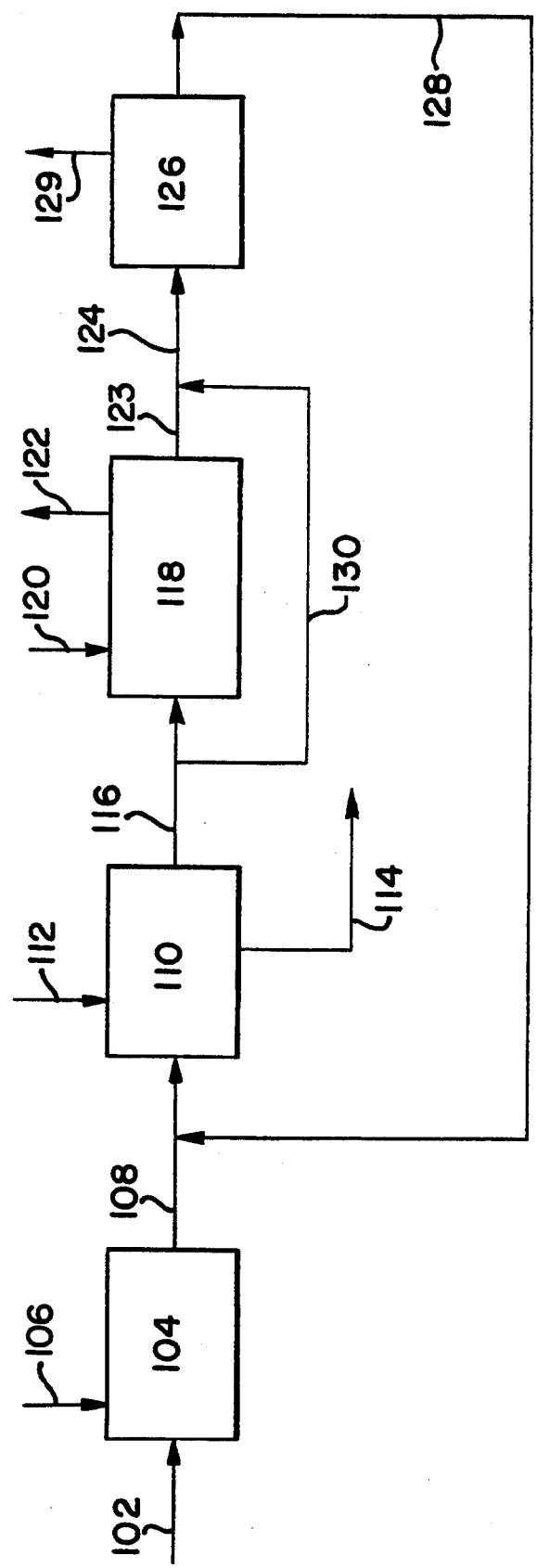
FIG. 3 depicts in flow chart format an alternative embodiment of the integrated process for the production of MTBE of the present invention.

Alternatively, as shown in FIG. 3, it is contemplated that the process of the present invention provides for a by-pass of a portion of the hydrocarbon feed around the extractive distillation unit. For ease of understanding, the parts of the process of FIG. 3 have been given part numbers similar to the corresponding parts of the process of FIG. 1, except in the 100 series. The use of a by-pass line 130 around the extractive distillation unit 118 results in the feed line 124 to the skeletal isomerization unit 126 comprising both the bypass stream 130 and the olefin enriched stream 123 from the extractive distillation unit.

The sequence of FIG. 3, comprising a by-pass of the extractive distillation with a portion of the MTBE synthesis effluent, is particularly useful in embodiments where the feed to the integrated MTBE process contains low concentrations of normal and isobutane. With low concentrations of normal and isobutane in the feed, it is desirable to by-pass the extractive distillation with a portion of the effluent from the MTBE synthesis unit since the paraffin purge stream is relatively small compared to the quantity of material to be processed. More-over, the use of the by-pass results in an increase in MTBE product. Olefin loss in the extractive distillation unit from olefins in the by-pass stream is avoided and the additional olefins are then converted to MTBE.

Figure 4:
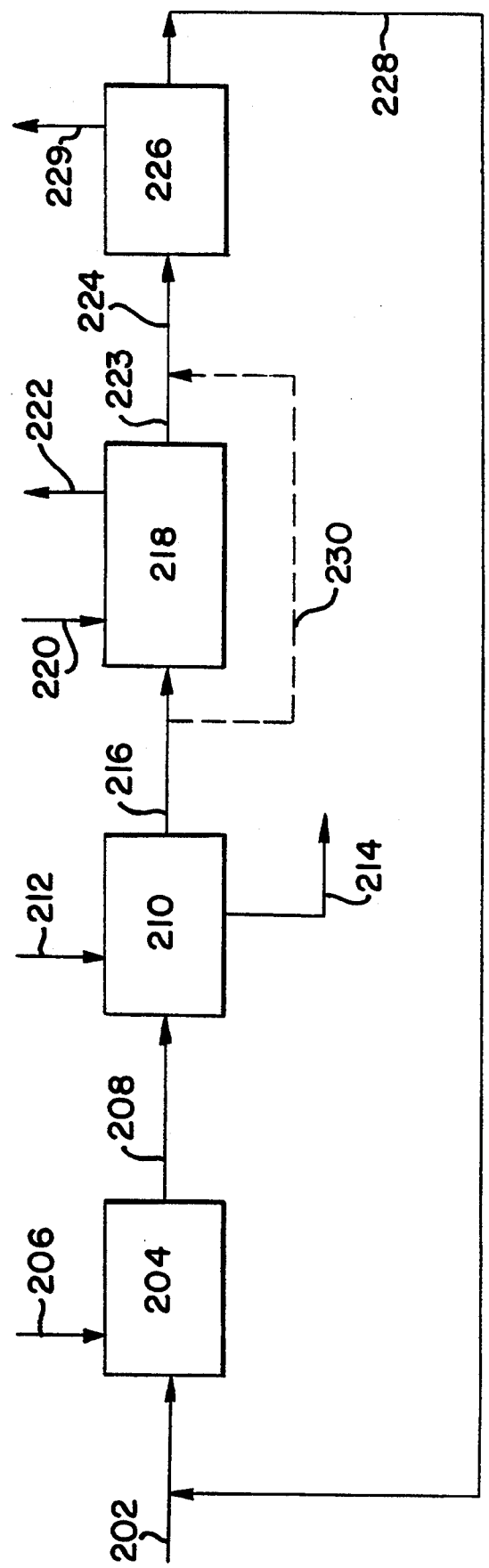
FIG. 4 depicts in flow chart format an alternative embodiment of the integrated process for the production of MTBE of the present invention.

Another alternative embodiment is shown in FIG. 4. For ease of understanding, the parts of the process of FIG. 4 have been given part numbers similar to the corresponding parts of the process of FIG. 3, including an optional by-pass stream, except in the 200 series. The process of FIG. 4 comprises directing the recycle stream 228 from the skeletal isomerization unit 226 to the feed stream 202 of the hydroisomerization unit 204. This embodiment is particularly useful where the skeletal isomerization catalysts isomerize a significant portion of the butene-2 hydrocarbons to butene-1. By recycling the effluent from the skeletal isomerization unit to the hydroisomerization unit, additional butene-2 is provided for the extractive distillation unit.

DESCRIPTION OF THE PREFERRED EMBODIMENTS

The following examples illustrate the present invention. They are not to be construed to limit the scope of the appended claims in any manner whatsoever.

EXAMPLE

Material balances were performed on a process according to the present invention comprising, in sequence, a hydroisomerization unit (operating at 77.8% conversion), an MTBE synthesis unit, an extractive distillation unit and a skeletal isomerization unit (operating at 37.4% n-butene conversion). For comparative purposes, processes without the extractive distillation, but with 15, 30 and 60% purge, respectively, were also analyzed. The results are set forth below in Tables 1–4. All values are reported in kg/hr.

TABLE 1

PROCESS WITH EXTRACTIVE DISTILLATION

| Component | Stream No. | | | | | | | | | | |
|---|---|---|---|---|---|---|---|---|---|---|---|
| | 2 | 6 | 8 | 8 + 28 | 16 | 24 | 28 | 22 | 12 | 14 | 29 |
| $H_2$ | 0 | 9 | 0 | 0 | 0 | 0 | 0 | 0 | 0 | 0 | 0 |
| Fuel Gas | 0 | 0 | 0 | 63 | 63 | 0 | 63 | 63 | 0 | 0 | 0 |
| $C_2$—$C_3$ Hydrocarbons | 20 | 0 | 20 | 565 | 565 | 0 | 545 | 565 | 0 | 0 | 0 |
| 1,3-butadiene | 84 | 0 | 0 | 0 | 0 | 0 | 0 | 0 | 0 | 0 | 0 |
| 1-butene | 5655 | 0 | 1260 | 2589 | 2589 | 2123 | 1329 | 466 | 0 | 0 | 0 |
| 2-butenes | 2795 | 0 | 7114 | 19001 | 19001 | 18989 | 11887 | 12 | 0 | 0 | 0 |
| i-butene | 8093 | 0 | 8093 | 14465 | 145 | 95 | 6372 | 50 | 0 | 0 | 0 |
| n + i-butane | 3255 | 0 | 3424 | 4073 | 4073 | 531 | 699 | 3542 | 0 | 0 | 0 |
| pentane | 53 | 0 | 53 | 53 | 0 | 0 | 0 | 0 | 0 | 53 | 0 |
| gasoline | 0 | 0 | 0 | 0 | 0 | 0 | 0 | 0 | 0 | 0 | 893 |
| fuel oil | 0 | 0 | 0 | 0 | 0 | 0 | 0 | 0 | 0 | 0 | 0 |
| methanol | 0 | 0 | 0 | 0 | 0 | 0 | 0 | 0 | 8209 | 41 | 0 |
| MTBE | 0 | 0 | 0 | 0 | 0 | 0 | 0 | 0 | 0 | 22488 | 0 |
| Total | 19955 | 9 | 19964 | 40809 | 26436 | 21738 | 20845 | 4698 | 8209 | 22582 | 893 |

Notes:
1. Minor by-products of MTBE reaction are not shown.
2. Material balance is on a water free basis.
3. Butene-2 isomerization to butene-1 in the skeletal isomerization reaction is not shown.

TABLE 2

PROCESS WITH 15 PERCENT PURGE

| Component | Stream No. | | | | | | | | | | | |
|---|---|---|---|---|---|---|---|---|---|---|---|---|
| | 2' | 6' | 8' | 8' + 28' | 16' | 24' | 28' | 22' | 27' | 29' | 12' | 14' |
| $H_2$ | 0 | 4 | 0 | 0 | 0 | 0 | 0 | 0 | 0 | 0 | 0 | 0 |
| Fuel Gas | 0 | 0 | 0 | 0 | 0 | 0 | 0 | 0 | 46 | 0 | 0 | 0 |
| $C_2$—$C_3$ Hydrocarbons | 20 | 0 | 20 | 20 | 20 | 17 | 0 | 3 | 416 | 0 | 0 | 0 |
| 1,3-butadiene | 84 | 0 | 0 | 0 | 0 | 0 | 0 | 0 | 0 | 0 | 0 | 0 |
| 1-butene | 5655 | 0 | 5675 | 12128 | 12128 | 10309 | 6453 | 1819 | 0 | 0 | 0 | 0 |
| 2-butenes | 2795 | 0 | 2838 | 6066 | 6066 | 5156 | 3228 | 910 | 0 | 0 | 0 | 0 |
| i-butene | 8093 | 0 | 8093 | 12796 | 124 | 105 | 4703 | 19 | 0 | 0 | 0 | 0 |
| n + i-butane | 3255 | 0 | 3280 | 22445 | 22445 | 19078 | 19165 | 3367 | 0 | 0 | 0 | 0 |
| pentane | 53 | 0 | 53 | 53 | 0 | 0 | 0 | 0 | 0 | 0 | 0 | 53 |
| gasoline | 0 | 0 | 0 | 0 | 0 | 0 | 0 | 0 | 0 | 654 | 0 | 0 |
| fuel oil | 0 | 0 | 0 | 0 | 0 | 0 | 0 | 0 | 0 | 0 | 0 | 0 |
| methanol | 0 | 0 | 0 | 0 | 0 | 0 | 0 | 0 | 0 | 0 | 7264 | 36 |
| MTBE | 0 | 0 | 0 | 0 | 0 | 0 | 0 | 0 | 0 | 0 | 0 | 19900 |
| Total | 19955 | 4 | 19959 | 53508 | 40783 | 34665 | 33549 | 6118 | 462 | 654 | 7264 | 19989 |

Notes:
1. Minor by-products of MTBE reaction are not shown.
2. Material balance is on a water-free basis.
3. Butene-2 isomerization to butene-1 in the skeletal isomerization reaction is not shown.

TABLE 3

PROCESS WITH 30 PERCENT PURGE

| Component | 2' | 6' | 8' | 8' + 28' | 16' | 24' | 28' | 22' | 27' | 29' | 12' | 14' |
|---|---|---|---|---|---|---|---|---|---|---|---|---|
| $H_2$ | 0 | 4 | 0 | 0 | 0 | 0 | 0 | 0 | 0 | 0 | 0 | 0 |
| Fuel Gas | 0 | 0 | 0 | 0 | 0 | 0 | 0 | 0 | 32 | 0 | 0 | 0 |
| $C_2$—$C_3$ Hydrocarbons | 20 | 0 | 20 | 20 | 20 | 14 | 0 | 6 | 287 | 0 | 0 | 0 |
| 1,3-butadiene | 84 | 0 | 0 | 0 | 0 | 0 | 0 | 0 | 0 | 0 | 0 | 0 |
| 1-butene | 5655 | 0 | 5575 | 10101 | 10101 | 7071 | 4426 | 3030 | 0 | 0 | 0 | 0 |
| 2-butenes | 2795 | 0 | 2838 | 5052 | 5052 | 3536 | 2214 | 1516 | 0 | 0 | 0 | 0 |
| i-butene | 8093 | 0 | 8093 | 11324 | 113 | 77 | 3231 | 34 | 0 | 0 | 0 | 0 |
| n + i-butane | 3255 | 0 | 3280 | 11132 | 11132 | 7792 | 7852 | 3340 | 0 | 0 | 0 | 0 |
| pentane | 53 | 0 | 53 | 53 | 0 | 0 | 0 | 0 | 0 | 0 | 0 | 53 |
| gasoline | 0 | 0 | 0 | 0 | 0 | 0 | 0 | 0 | 0 | 448 | 0 | 0 |
| fuel oil | 0 | 0 | 0 | 0 | 0 | 0 | 0 | 0 | 0 | 0 | 0 | 0 |
| methanol | 0 | 0 | 0 | 0 | 0 | 0 | 0 | 0 | 0 | 0 | 6427 | 32 |
| MTBE | 0 | 0 | 0 | 0 | 0 | 0 | 0 | 0 | 0 | 0 | 0 | 17606 |
| Total | 19955 | 4 | 19959 | 37682 | 26418 | 18490 | 17723 | 7928 | 319 | 448 | 6427 | 17691 |

Notes:
1. Minor by-products of MTBE reaction are not shown.
2. Material balance is on a water-free basis.
3. Butene-2 isomerization to butene-1 in the skeletal isomerization reaction is not shown.

TABLE 4

PROCESS WITH 60 PERCENT PURGE

| Component | 2' | 6' | 8' | 8' + 28' | 16' | 24' | 28' | 22' | 27' | 29' | 12' | 14' |
|---|---|---|---|---|---|---|---|---|---|---|---|---|
| $H_2$ | 0 | 4 | 0 | 0 | 0 | 0 | 0 | 0 | 0 | 0 | 0 | 0 |
| Fuel Gas | 0 | 0 | 0 | 0 | 0 | 0 | 0 | 0 | 14 | 0 | 0 | 0 |
| $C_2$—$C_3$ Hydrocarbons | 20 | 0 | 20 | 20 | 20 | 8 | 0 | 12 | 125 | 0 | 0 | 0 |
| 1,3-butadiene | 84 | 0 | 0 | 0 | 0 | 0 | 0 | 0 | 0 | 0 | 0 | 0 |
| 1-butene | 5655 | 0 | 5675 | 7571 | 7571 | 3028 | 1896 | 4543 | 0 | 0 | 0 | 0 |
| 2-butenes | 2795 | 0 | 2838 | 3786 | 3786 | 1514 | 948 | 2272 | 0 | 0 | 0 | 0 |
| i-butene | 8093 | 0 | 8093 | 9480 | 95 | 37 | 1387 | 58 | 0 | 0 | 0 | 0 |
| n + i-butane | 3255 | 0 | 3280 | 5509 | 5509 | 2204 | 2229 | 3305 | 0 | 0 | 0 | 0 |
| pentane | 53 | 0 | 53 | 53 | 0 | 0 | 0 | 0 | 0 | 0 | 0 | 53 |
| gasoline | 0 | 0 | 0 | 0 | 0 | 0 | 0 | 0 | 0 | 192 | 0 | 0 |
| fuel oil | 0 | 0 | 0 | 0 | 0 | 0 | 0 | 0 | 0 | 0 | 0 | 0 |
| methanol | 0 | 0 | 0 | 0 | 0 | 0 | 0 | 0 | 0 | 0 | 5380 | 26 |
| MTBE | 0 | 0 | 0 | 0 | 0 | 0 | 0 | 0 | 0 | 0 | 0 | 14738 |
| Total | 19955 | 4 | 19959 | 26419 | 16981 | 6791 | 6460 | 10190 | 139 | 192 | 5380 | 14818 |

Notes:
1. Minor by-products of MTBE reaction are not shown.
2. Material balance is on a water-free basis.
3. Butene-2 isomerization to butene-1 in the skeletal isomerization reaction is not shown.

In Tables 2–4, the primed stream numbers generally correspond to the stream numbers in FIG. 1. Further, stream no. 22' refers to a purge stream removed from the MTBE synthesis unit effluent which includes both paraffins and valuable olefins; stream no. 24' refers to the stream which is fed to the skeletal isomerization unit and comprises the MTBE synthesis effluent minus the purge stream 22'; stream 27' refers to a light hydrocarbon takeoff from the skeletal isomerization unit; and stream 29' refers to a heavy hydrocarbon (gasoline) takeoff from the skeletal isomerization unit. Additionally, unit 4' is normally a selective hydrogenation unit which would convert butadiene to olefins but would not perform the olefin isomerization. See FIG. 2.

For convenience, the results of the material balances are summarized below in Table 5.

TABLE 5

Summary of Results

| Process | MTBE Produced | MTBE Feed | SI Feed |
|---|---|---|---|
| Table 1 - with extractive distillation | 22488 | 40809 | 21738 |
| Table 2 - 15% Purge | 19900 | 53508 | 34665 |
| Table 3 - 30% Purge | 17606 | 37682 | 18490 |
| Table 4 - 60% Purge | 14738 | 26419 | 6791 |

SI - Skeletal Isomerization

From Table 5 it can be seen that the process according to the appended claims with the extractive distillation unit provides significant advantages over the processes without the extractive distillation step. As compared to the process employing the 15% purge, the process of the present invention provides improved yields of MTBE and significantly reduces the feed to the MTBE synthesis unit and skeletal isomerization unit. As compared to the process with the 30% purge, while the feed rates to the MTBE synthesis and skeletal isomerization units are similar to the process of the present invention, the process of the present invention provides a significant increase in MTBE yield. Further, as compared to the process with the 60% purge, while the 60% purge process has reduced feed rates to the MTBE synthesis unit and the skeletal isomerization unit, the MTBE yield for the 60% purge process is only abut 66% of the MTBE yield of the present process.

Accordingly, it can be seen that the process of the present invention concurrently provides both increased yields and reduced feed rates to the MTBE synthesis and skeletal isomerization units.

Many variations of the present invention will suggest themselves to those skilled in the art in light of the above-detailed description. For example, the specific conditions and catalysts for each of the process steps may be varied. Further, molecular sieve separation and selective membrane separation units may be employed in place of or in addition to the extractive distillation unit; and selective hydrogenation units may be employed in place of or in addition to the hydroisomerization unit. All such obvious modifications are within the full intended scope of the appended claims.

All of the above-referenced patents and publications are hereby incorporated by reference.

We claim:

1. An integrated process for the production of methyl tertiary butyl ether from a mixed $C_4$ hydrocarbon feedstock comprising ethyl acetylene, vinyl acetylene, 1,3-butadiene, 1,2-butadiene, isobutylene, cis-2-butene, trans-2-butene, 1-butene, isobutane, and n-butane, said process comprising passing said feedstock through zones of hydroisomerization, methyl tertiary butyl ether synthesis, paraffin/olefin separation and skeletal isomerization; wherein:

said hydroisomerization zone comprises catalytically converting most of the ethyl acetylene, vinyl acetylene, 1,3-butadiene and 1,2-butadiene to butenes from said mixed $C_4$ hydrocarbon feedstock;

and converting at least a portion of the 1-butene from said mixed $C_4$ hydrocarbon feedstock to 2-butenes in the presence of a catalyst comprising at least one hydrogenating metal and a moderately acidic carrier at a temperature ranging from about 40° C. to about 400° C. and a pressure ranging from about 1 to 100 bars;

said methyl tertiary butyl ether synthesis zone comprises reacting isobutylene from said mixed $C_4$ hydrocarbon feedstock and the effluent from said skeletal isomerization zone with methanol in the presence of an acid type ion exchange resin catalyst at a temperature ranging from about 60° F. to about 300° F. and a pressure ranging from about 80 to 400 psig and withdrawing a methyl tertiary butyl ether product;

said paraffin/olefin separation zone comprises separating at least a portion of the $C_4$ paraffins, from said mixed $C_4$ hydrocarbon feedstock, from the $C_4$ olefins and withdrawing said separated $C_4$ paraffins;

said skeletal isomerization zone comprises catalytically converting at least a portion of the 2-butenes from the mixed $C_4$ hydrocarbon feedstock and the effluent from the hydroisomerization zone to isobutylene in the presence of an acidic catalyst at a pressure of about atmospheric and a temperature ranging from about 600° F. to about 1100° F. to produce an isobutylene-rich effluent; and recycling the isobutylene-rich effluent to said hydroisomerization zone or said methyl tertiary butyl ether synthesis zone.

2. A process as defined in claim 1 wherein said mixed $C_4$ hydrocarbon feedstock is a portion of the effluent from a fluid catalytic cracking process.

3. A process as defined in claim 1 wherein said mixed $C_4$ hydrocarbon feedstock is a portion of the effluent from an olefins production plant.

4. A process as defined in claim 1 which further comprises an upstream butadiene extraction unit to remove a portion of the 1,3-butadiene, and 1,2-butadiene components from said mixed $C_4$ hydrocarbon feedstock.

5. A process as defined in claim 1 wherein said hydrogenating metal comprises platinum, palladium and/or nickel.

6. A process as defined in claim 1 wherein said hydroisomerization is carried out at a space velocity ranging from about 0.5 to 20 kg hydrocarbon feed/kg catalyst hour.

7. A process as defined in claim 6 wherein the hydroisomerization is carried out in a mixed phase at a temperature ranging from about 40° to about 150° C., a pressure ranging from about 10 to about 40 bar and a space velocity ranging from about 1 to about 15 kg feed/kg catalyst hour.

8. A process as defined in claim 1 wherein said acid ion exchange resin is selected from sulfonated type coals, phenol formaldehyde resins reacted with sulfuric acids, sulfonated resinous polymers of cumarone-indene with cyclopentadiene, sulfonated divinylbenzene polystyrene copolymers and mixtures of any of the foregoing.

9. A process as defined in claim 8 wherein said acid type ion exchange resin comprises a sulfonated divinylbenzene polystyrene copolymer.

10. A process as defined in claim 1 wherein said methyl tertiary butyl ether synthesis is carried out at a mole ratio of methanol to isobutylene of from about 0.05 to 10.

11. A process as defined in claim 10 wherein said synthesis is carried out at a mole ratio ranging from about 0.1 to about 5 and a temperature ranging from about 100° F. to about 250° F.

12. A process as defined in claim 1 wherein said paraffin/olefin separation comprises separating the $C_4$ paraffins from the $C_4$ olefins in the presence of a solvent in an extractive distillation unit.

13. A process as defined in claim 12 wherein the solvent, optionally in the presence of a water diluent, for the extractive distillation step is selected from tetrahydrofuran, diethyl ketone, diethyl carbonate, methyl ethyl ketone, pentanedione, cyclopentanone, acetone, butyronitrile, acetyl piperidine, acetophenone, pyridine, diethyl oxalate, propionitrile, dimethyl acetamide, n-methyl pyrrolidone, acetonyl acetone, tetrahydrofurfuryl alcohol, dimethyl sulfolane, dimethyl cyanamide, methyl carbitol, dimethyl formamide, methyl cellosolve, furfural, acetonitrile, ethylene chlorhydrin, gamma-butyrolactone, methanol, beta-chloropropionitrile, pyrrolidone, propylene carbonate, nitromethane, ethylene diamine and mixtures of any of the foregoing.

14. A process as defined in claim 13 wherein said solvent comprises acetonitrile, optionally in the presence of a water diluent.

15. A process as defined in claim 1 wherein said isobutylene-rich effluent from the skeletal isomerization zone is recycled to the methyl tertiary butyl ether zone.

16. A process as defined in claim 1 wherein said isobutylene-rich effluent from the skeletal isomerization zone is recycled to the hydroisomerization zone.

17. An integrated process for the production of methyl tertiary butyl ether from a mixed $C_4$ hydrocarbon feedstock comprising ethyl acetylene, vinyl acetylene, 1,3-butadiene, 1,2-butadiene, isobutylene, cis-2-butene, trans-2-butene, 1-butene, isobutane and n-butane, said process comprising the following process steps conducted in sequence:

(a) catalytically hydrogenating most of the ethyl acetylene vinyl acetylene, 1,3-butadiene and 1,2-butadiene to butenes and catalytically converting at least a portion of the 1-butene to 2-butenes in the presence of a catalyst comprising at least one hydrogenating metal and a moderately acidic carrier at a temperature ranging from about 40° C. to about 400° C. and a pressure ranging from about 1 to about 100 bars in a hydroisomerization zone to produce a hydrogenated mixed $C_4$ hydrocarbon feedstock comprising isobutylene, 1-butene, 2-butenes and $C_4$ paraffins;

(b) reacting isobutylene in the hydrogenated mixed $C_4$ hydrocarbon feedstock with methanol in a methyl tertiary butyl ether synthesis zone in the presence of an acid type ion exchange resin catalyst at a temperature ranging from about 60° F. to about 300° F. and a pressure ranging from about 80 to 400 psig to produce a methyl tertiary ether-rich product effluent and a synthesis by-product effluent comprising $C_4$ paraffins and $C_4$ olefins;

(c) separating the $C_4$ paraffins from the $C_4$ olefins in said synthesis by-product effluent in a paraffin/olefin separation zone to produce a $C_4$ paraffin-rich effluent and a $C_4$ olefin-rich effluent comprising 1-butene and 2-butenes;

(d) catalytically converting at least a portion of the 2-butenes in said $C_4$ olefin rich effluent to isobutylene in a skeletal isomerization zone in the presence of an acidic catalyst at a pressure of about atmospheric and a temperature ranging from about 600° F. to about 1100° F. to produce a skeletal isomerized effluent; and (e) recycling said skeletal isomerized effluent to step (a) or step (b).

18. A process as defined in claim 17 wherein said mixed $C_4$ hydrocarbon feedstock is a portion of the effluent from a fluid catalytic cracking process.

19. A process as defined in claim 17 wherein said mixed $C_4$ hydrocarbon feedstock is a portion of the effluent from an olefins production plant.

20. A process as defined in claim 17 which further comprises an upstream butadiene extraction unit to remove a portion of the 1,3-butadiene and/or 1,2-butadiene components from said mixed $C_4$ hydrocarbon feedstock.

21. A process as defined in claim 17 wherein said hydrogenating metal comprises platinum, palladium and/or nickel.

22. A process as defined in claim 21 wherein said hydroisomerization is carried out at a space velocity ranging from about 0.5 to 20 kg hydrocarbon feed/kg catalyst hour.

23. A process as defined in claim 22 wherein the hydroisomerization is carried out in a mixed phase at a temperature ranging from about 40° to about 150° C., a pressure ranging from about 10 to about 40 bar and a space velocity ranging from about 1 to about 15 kg feed/kg catalyst hour.

24. A process as defined in claim 17 wherein said acid type ion exchange resin is selected from sulfonated coals, phenol formaldehyde resins reacted with sulfuric acids, sulfonated resinous polymers of cumarone-indene with cyclopentadiene, sulfonated divinylbenzene polystyrene copolymers and mixtures of any of the foregoing.

25. A process as defined in claim 24 wherein said acid type ion exchange resin comprises a sulfonated divinylbenzene polystyrene copolymer.

26. A process as defined in claim 25 wherein said methyl tertiary butyl ether synthesis is carried out at a mole ratio of methanol to isobutylene of from about 0.05 to 10.

27. A process as defined in claim 26 wherein said methyl tertiary butyl ether synthesis is carried out at a mole ratio ranging from about 0.1 to about 5 and a temperature ranging from about 100° F. to about 250° F.

28. A process as defined in claim 17 wherein said paraffin/olefin separation comprises separating the $C_4$ paraffins from the $C_4$ olefins in the present of a solvent in an extractive distillation unit.

29. A process as defined in claim 28 wherein the solvent, optionally in the presence of a water diluent, for the extractive distillation step is selected from tetrahydrofuran, diethyl ketone, diethyl carbonate, methyl ethyl ketone, pentanedione, cyclopentanone, acetone, butyronitrile, acetyl piperidine, acetophenone, pyridine, diethyl oxalate, propionitrile, dimethyl acetamide, n-methyl pyrrolidone, acetonyl acetone, tetrahydrofurfuryl alcohol, dimethyl sulfolane, dimethyl cyanamide, methyl carbitol, dimethyl formamide, methyl cellosolve, furfural, acetonitrile, ethylene chlorhydrin, gamma-butyrolactone, methanol, beta-chloropropionitrile, pyrrolidone, propylene carbonate, nitromethane, ethylene diamine and mixtures of any of the foregoing.

30. A process as defined in claim 29 wherein said solvent comprises acetonitrile, optionally in the presence of a water diluent.

31. A process as defined in claim 28 wherein said extractive distillation step comprises passing said synthesis effluent through an extractive distillation tower wherein said synthesis effluent is separated into an overhead purge stream comprising $C_3$ and lighter boiling hydrocarbons, isobutane and n-butane and a stripper overhead stream comprising mostly cis-2-butene, trans-2-butene and 1-butene.

32. A process as defined in claim 28 further comprising by-passing a portion of the synthesis effluent around the extractive distillation step.

33. A process as defined in claim 17 wherein the effluent from the skeletal isomerization zone is recycled to the methyl tertiary butyl ether synthesis zone.

34. A process as defined in claim 17 wherein the effluent from the skeletal isomerization zone is recycled to the hydroisomerization zone.

* * * * *